United States Patent
Engell et al.

(10) Patent No.: US 12,162,009 B2
(45) Date of Patent: Dec. 10, 2024

(54) SOLID PHASE PURIFICATION

(71) Applicant: GE Healthcare Limited, Buckinghamshire (GB)

(72) Inventors: Torgrim Engell, Oslo (NO); Alexander Jackson, Amersham Place (GB); Imtiaz Ahmed Khan, Buckinghamshire (GB); Alan P. Clarke, Nydalen (NO); Graeme McRobbie, Buckinghamshire (GB); Julian Grigg, Buckinghamshire (GB)

(73) Assignee: GE Healthcare Limited, Buckinghamshire (GB)

( * ) Notice: Subject to any disclaimer, the term of this patent is extended or adjusted under 35 U.S.C. 154(b) by 960 days.

(21) Appl. No.: 17/043,328

(22) PCT Filed: Mar. 29, 2019

(86) PCT No.: PCT/EP2019/058112
§ 371 (c)(1),
(2) Date: Sep. 29, 2020

(87) PCT Pub. No.: WO2019/185933
PCT Pub. Date: Oct. 3, 2019

(65) Prior Publication Data
US 2021/0023558 A1    Jan. 28, 2021

(30) Foreign Application Priority Data
Mar. 29, 2018   (GB) ..................................... 1805253

(51) Int. Cl.
*B01L 3/00*       (2006.01)
*B01J 19/00*     (2006.01)
(Continued)

(52) U.S. Cl.
CPC ....... *B01L 3/502753* (2013.01); *B01J 19/004* (2013.01); *C07B 59/002* (2013.01);
(Continued)

(58) Field of Classification Search
None
See application file for complete search history.

(56) References Cited

U.S. PATENT DOCUMENTS

| | | |
|---|---|---|
| 6,172,207 B1 | 1/2001 | Damhaut et al. |
| 7,642,373 B2 | 1/2010 | Wadsworth et al. |

(Continued)

FOREIGN PATENT DOCUMENTS

| | | |
|---|---|---|
| CN | 1898184 A | 1/2007 |
| CN | 102858752 A | 1/2013 |

(Continued)

OTHER PUBLICATIONS

Office Action received in Japanese Application No. 2020-552212 dated Apr. 12, 2023, with translation, 7 pages.

(Continued)

*Primary Examiner* — Jyoti Nagpaul
(74) *Attorney, Agent, or Firm* — MCANDREWS HELD & MALLOY, LTD

(57) ABSTRACT

The present invention provides a method for the synthesis of an injectable composition comprising a [$^{18}$F]-labelled pyridaben derivative that is amenable to automation. In particular, the method of the present invention comprises a method of purification carried out by means of solid phase extraction (SPE) alone.

21 Claims, 4 Drawing Sheets

(51) Int. Cl.
  *C07B 59/00* (2006.01)
  *C07D 237/16* (2006.01)
(52) U.S. Cl.
  CPC .... *C07D 237/16* (2013.01); *B01L 2200/0631* (2013.01); *C07B 2200/05* (2013.01)

(56) References Cited

U.S. PATENT DOCUMENTS

| | | |
|---|---|---|
| 9,061,996 B2 | 6/2015 | Mantzilas et al. |
| 9,408,927 B2 | 8/2016 | Robinson et al. |
| 9,603,951 B2 | 3/2017 | Lazewatsky et al. |
| 9,687,571 B2 | 6/2017 | Castner et al. |
| 2014/0328757 A1 | 11/2014 | Castner et al. |
| 2015/0175553 A1 | 6/2015 | Wouters et al. |
| 2017/0128597 A1 | 5/2017 | Dyrstad et al. |
| 2019/0055207 A1 | 2/2019 | Okumura et al. |

FOREIGN PATENT DOCUMENTS

| | | |
|---|---|---|
| CN | 103249698 A | 8/2013 |
| CN | 103958049 A | 7/2014 |
| CN | 107261159 A | 10/2017 |
| JP | H11508923 A | 8/1999 |
| JP | 2011513306 A | 4/2011 |
| JP | 201781847 A | 5/2017 |
| JP | 2017520550 A | 7/2017 |
| WO | 2011097649 A2 | 8/2011 |
| WO | 2013079578 A1 | 6/2013 |
| WO | WO2013/079578 * | 6/2013 |

OTHER PUBLICATIONS

Great Britain Search Report received in Application No. GB1805253.0 dated Nov. 20, 2018, 4 pages.
Search report received in Application No. PCT/EP2019/058112 dated May 24, 2019, 12 pages.
Office Action received in Chinese Application No. 201980036252.0 dated Oct. 26, 2022, with translation, 24 pages.

* cited by examiner

SOLID PHASE PURIFICATION

CROSS REFERENCE TO REPLATED APPLICATIONS

This application is a filing under 35 U.S.C. § 371 of international application number PCT/EP2019/058112, filed Mar. 29, 2019, which claims priority to application number GB 1805253.0 filed on Mar. 29, 2018, the entire disclosures of each of which are hereby incorporated by reference.

TECHNICAL FIELD OF THE INVENTION

The present invention relates to diagnostic imaging agents useful for positron emission tomography (PET) imaging as well as to improved means for producing such imaging agents. More specifically, the present invention is directed to method of purifying a crude [$^{18}$F]-labelled pyridaben derivative which in turn can then be formulated into a composition suitable for injection for myocardial perfusion imaging and methods and devices for preparing same. More specifically, the present invention is directed to the automated synthesis and purification of a [$^{18}$F]-labelled pyridaben derivative by means of solid phase extraction (SPE).

DESCRIPTION OF RELATED ART

[$^{18}$F]-labelled pyridaben derivatives are known that find use in determining the presence or absence of a cardiovascular disease or condition in a subject. Methods for the synthesis of these [$^{18}$F]-labelled pyridaben derivatives are described in WO2011097649 A2 and comprise nucleophilic [$^{18}$F]-fluorination of an imaging agent precursor to form an imaging agent. The synthesis of an injectable composition comprising the compound [$^{18}$F]-flurpiridaz ([$^{18}$F]-FPZ) is described wherein the method comprises nucleophilic [$^{18}$F]-fluorination of a tosylate precursor compound, dilution with water followed by high-performance liquid chromatography (HPLC) purification.

Finding a purification method for [$^{18}$F]-FPZ that avoids HPLC is highly desirable and would result in easier accessibility for commercial application. However, efforts to achieve this up to now have been hindered by the presence of an acetyl impurity that elutes very close to the desired product that to date can only be precisely removed using a purification method comprising HPLC.

SUMMARY OF THE INVENTION

The present invention provides a method comprising:
(a) reacting in acetonitrile a precursor compound of Formula I:

BTM-LINKER-LG    (I)

wherein:
BTM is a biological targeting moiety;
LINKER is an alkylene or an alkoxyalkylene; and,
LG is a sulfonate-containing leaving group
with $^{18}$F-fluoride to obtain a crude reaction mixture comprising an $^{18}$F-labelled compound of Formula II:

BTM-LINKER-$^{18}$F    (II)

wherein BTM and LINKER are as defined for Formula I;
(b) diluting the crude reaction mixture obtained in step (a) to obtain a diluted crude reaction mixture;
(c) purifying the diluted crude reaction mixture obtained in step (b) by means of one or more solid phase extraction (SPE) cartridges to obtain a purified compound of Formula II where said purifying comprises the sequential steps of:
(i) transferring said diluted crude reaction mixture to an SPE cartridge;
(ii) optionally passing water through said SPE cartridge;
(iii) passing a wash solution comprising an organic solvent through said SPE cartridge;
(iv) optionally passing water through said SPE cartridge in order to remove said organic solvent; and,
(v) passing an elution solution comprising ethanol through said SPE cartridge to elute said compound of Formula I from said SPE cartridge.
wherein step (b) includes adding a hydrolysing reagent to said crude reaction mixture and/or said water of step (ii) and/or step (iv) comprises a hydrolysing reagent.

In another aspect the present invention provides a cassette for carrying out the method as defined in claim 1 comprising:
i) a vessel containing the precursor compound as defined herein;
ii) a vessel containing water;
iii) one or more SPE cartridges;
iv) a vessel containing a solution comprising an organic solvent;
v) a vessel containing a solution comprising ethanol;
vi) a vessel containing a hydrolysing reagent;
vii) a reaction vessel;
viii) means for eluting the vessel of (i) with a suitable source of $^{18}$F;
ix) means to transfer the precursor compound and suitable source of $^{18}$F to the reaction vessel;
x) means to transfer the crude reaction mixture as defined herein to said one or more SPE cartridges;
xi) means to selectively transfer said water, said solution comprising an organic solvent and said solution comprising ethanol to said one or more SPE cartridges; and,
xii) means to transfer said purified compound of Formula II as defined herein to a product collection vial.

The method and cassette of the invention are particularly useful where the crude reaction mixture includes one or more impurities have very similar chromatographic elution times. Purification using SPE alone is permitted such that the requirement for HPLC in the purification process is obviated.

DETAILED DESCRIPTION OF THE PREFERRED EMBODIMENTS

Figure 1:
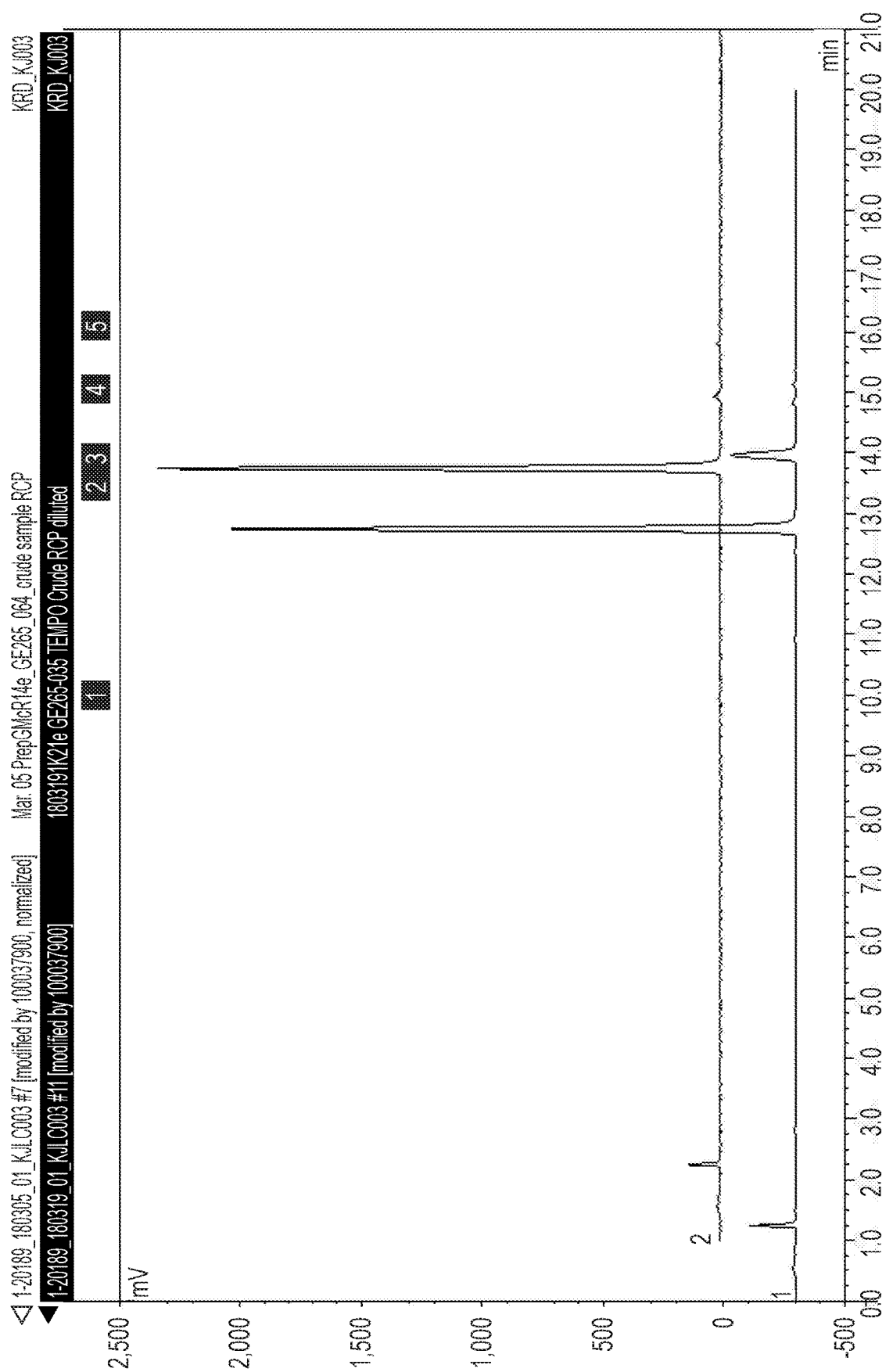
FIG. 1: Comparison of crude product with (top) and without (bottom) the addition of (2,2,6,6-Tetramethylpiperidin-1-yl)oxyl (TEMPO) to the labelling reaction.

To more clearly and concisely describe and point out the subject matter of the claimed invention, definitions are provided hereinbelow for specific terms used throughout the present specification and claims. Any exemplification of specific terms herein should be considered as a non-limiting example.

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

A "precursor compound" comprises a non-radioactive derivative of a radiolabelled compound, designed so that chemical reaction with a convenient chemical form of an in vivo-detectable label occurs site-specifically; can be conducted in the minimum number of steps (ideally a single step); and without the need for significant purification (ideally no further purification), to give the desired in vivo imaging agent. Such precursor compounds are synthetic and can conveniently be obtained in good chemical purity.

By the term "biological targeting moiety" (BTM) is meant a compound which, after administration, is taken up selectively or localises at a particular site of the mammalian body in vivo. Such sites may for example be implicated in a particular disease state or be indicative of how an organ or metabolic process is functioning.

The term "alkylene" refers to the bivalent group —(CH$_2$)$_n$— wherein n is preferably an integer from 1-6.

The term "alkoxyalkylene" means an alkylene as defined above comprising an ether linkage, where the term "ether linkage" refers to the group —C—O—C—.

The term "leaving group" refers to an atom or group of atoms that is displaced as a stable species during a substitution or displacement radiofluorination reaction. Suitable leaving groups for the present invention are sulfonate-containing leaving groups, where "sulfonate" means —SO$_3$.

The term "$^{18}$F-fluoride" refers to $^{18}$F-fluoride in a chemical form suitable for displacing LG of Formula I in a nucleophilic substitution reaction to result in a compound of Formula II. $^{18}$F-fluoride is normally obtained as an aqueous solution from the nuclear reaction $^{18}$O (p,n)$^{18}$F and is made reactive by the addition of a cationic counterion and the subsequent removal of water. Suitable cationic counterions should possess sufficient solubility within the anhydrous reaction solvent to maintain the solubility of $^{18}$F$^-$. Suitable counterions include large but soft metal ions such as rubidium or caesium, potassium complexed with a cryptand such as Kryptofix™ 222 (K222), or tetraalkylammonium salts. A suitable tetraalkylammonium salt is tetrabutylammonium hydrogen carbonate. A detailed discussion of well-known $^{18}$F labelling techniques can be found in Chapter 6 of the "Handbook of Radiopharmaceuticals" (2003; John Wiley and Sons: M. J. Welch and C. S. Redvanly, Eds.).

The term "solid phase extraction (SPE)" refers to the well-known sample preparation process by which compounds in a solution are separated from each other based on their respective affinities for a solid (the "solid phase", or "stationary phase") through which the sample is passed and the solvent (the "mobile phase" or "liquid phase") in which they are dissolved. The result is that a compound of interest is either retained on the solid phase or in the mobile phase. The portion that passes through the solid phase is collected or discarded, depending on whether it contains the compound of interest. If the portion retained on the stationary phase includes the compound of interest, it can then be removed from the stationary phase for collection in an additional step, in which the stationary phase is rinsed with another solution known as an "eluent". For the present invention SPE is suitably carried out using at least one "SPE cartridge" (also often referred to as an "SPE column"), a variety of which are readily available commercially and typically as a column packed with solid phase. Most known solid phases are based on silica that has been bonded to a specific functional group, e.g. hydrocarbon chains of variable length (suitable for reverse-phase SPE), quaternary ammonium or amino groups (suitable for anion exchange), and sulfonic acid or carboxyl groups (suitable for cation exchange). SPE in the context of the present invention specifically excludes HPLC. In one embodiment two SPE cartridges fluidly connected in series are used in the present invention.

The "organic solvent" suitably comprises a solvent known to those of skill in the art for SPE elution, for example tetrahydrofuran (THF), ethyl acetate and dichloromethane (DCM), dimethylformamide (DMF), acetonitrile (MeCN), dimethyl sulfoxide (DMSO), acetic acid, t-butanol, isopropanol, n-propanol, ethanol (EtOH) and methanol (MeOH). The organic solvent may be provided as an aqueous solution of said solvent.

The term "hydrolysing reagent" refers to a reagent capable of hydrolysis wherein "hydrolysis" is a technical term well known to those of skill in the art, i.e. a reaction involving the breaking of a bond in a molecule using water, where the reaction mainly occurs between an ion and water molecules and often changes the pH of a solution. In chemistry, there are three main types of hydrolysis: salt hydrolysis, acid hydrolysis, and base hydrolysis.

In one embodiment of the invention said BTM is a small molecule. The small molecule in one embodiment is an analogue of pyridaben. Methods to obtain suitable pyridaben analogues are known in the art.

In one embodiment certain compounds of Formula I can be obtained following or adapting the processes described in WO2011097649 A2, starting with etherification of the starting compounds comprising formulae:

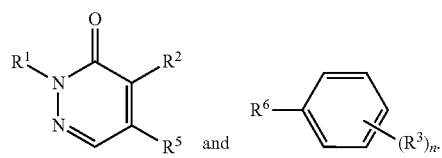

where n is 1, 2, 3, 4, or 5; R$^1$ is alkyl, optionally substituted; R$^2$ is hydrogen or halide; R$^3$ can be the same or different and are alkyl, heteroalkyl, or a carbonyl-containing group, each optionally substituted, R$^5$ is hydroxyl or halide; and R$^6$ is alkyl, heteroalkyl, or a carbonyl-containing group, each optionally substituted, wherein, when R$^5$ is hydroxyl, at least one of R$^6$ and R$^3$ comprises a leaving group; or wherein R$^5$ is halide, at least one of R$^6$ or R$^3$ comprises a hydroxyl, to produce a compound comprising formula:

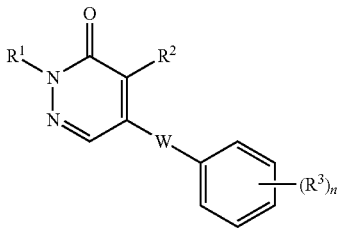

wherein W is alkyl or heteroalkyl, optionally substituted; $R^1$ is alkyl, optionally substituted; $R^2$ is hydrogen or halide; each $R^3$ can be the same or different and is alkyl optionally substituted with hydroxyl or heteroalkyl optionally substituted with hydroxyl; wherein at least one $R^3$ comprises hydroxyl; and n is 1, 2, 3, 4, or 5; $R^1$ is alkyl, optionally substituted; $R^2$ is hydrogen or halide; $R^3$ can be the same or different and are alkyl, heteroalkyl, or a carbonyl-containing group, each optionally substituted. Then reacting this compound with a sulfonate-containing species such that at least one $R^3$ is converted to alkyl substituted with a sulfonate-containing group or heteroalkyl substituted with a sulfonate-containing group. This sulfonate-containing compound is a precursor compound of Formula I of the present invention. The sulfonate-containing precursor can then be reacted with $^{18}$F-fluoride to obtain compounds of Formula II of the present invention.

In one embodiment of the invention, said precursor compound is a compound of Formula Ia:

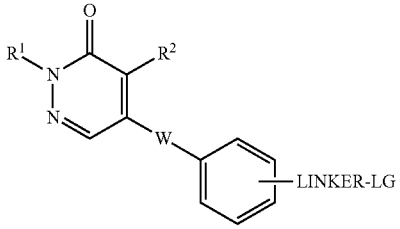

(Ia)

and said $^{18}$F-labelled compound is a compound of Formula IIa:

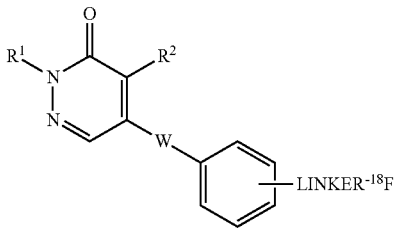

(Ia)

wherein:
$R^1$ is an optionally substituted $C_{1-6}$ alkyl;
$R^2$ is hydrogen or halo;
W is an optionally substituted alkylene or heteroalkylene;
LINKER and LG are as defined in claim 1.

In one embodiment $R^1$ of Formula Ia and Formula IIa is $C_{1-6}$ alkyl.

In one embodiment $R^1$ of Formula Ia and Formula IIa is methyl, ethyl, propyl, n-butyl, s-butyl, or t-butyl.

In one embodiment $R^2$ of Formula Ia and Formula IIa is halo.

In one embodiment $R^2$ of Formula Ia and Formula IIa is chloro.

In one embodiment W of Formula Ia and Formula IIa is heteroalkylene.

In one embodiment W of Formula Ia and Formula IIa alkoxyalkylene.

In one embodiment of the invention, said compound of Formula I is a compound of Formula Ib:

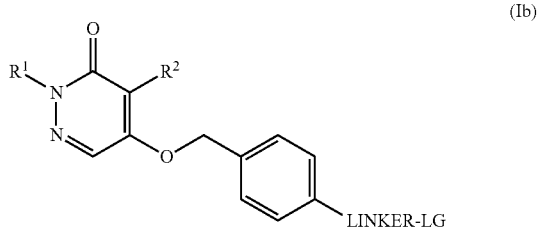

(Ib)

and said compound of Formula II is a compound of Formula IIb:

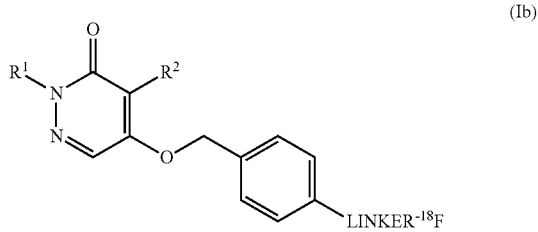

(Ib)

wherein $R^1$, $R^2$, LINKER and LG are as variously defined herein for Formula I and Formula II.

In one embodiment of the invention, said compound of Formula I is:

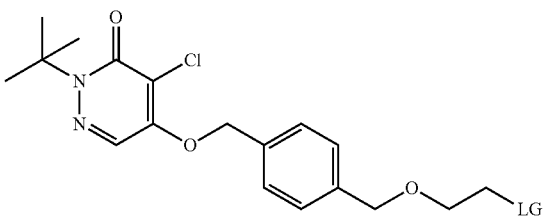

wherein LG is as variously defined herein;
and said compound of Formula II is:

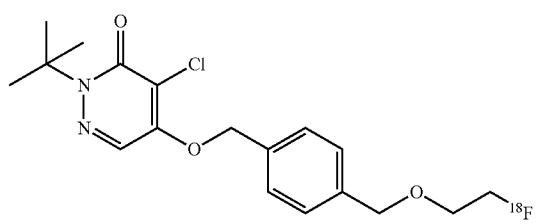 [SMILES: CC(C)(C)n1ncc(OCc2ccc(COCC[18F])cc2)c(Cl)c1=O]

In one embodiment of the invention LG is selected from mesylate, tosylate, triflate, nosylate, or 1,2-cyclic sulfate.

In one embodiment of the invention LG is tosylate.

In one embodiment of the invention, said wash solution comprising an organic solvent of step (c)(iii) comprises 20-80% of said organic solvent in water. In certain embodiments, as will be known to a person skilled in the art, the mobile phase used with the SPE cartridge will depend on choice of SPE cartridge. For example, in one embodiment where the SPE is an Affinisep polymer, aqueous acetonitrile is a suitable organic solvent, for step (iii), a non-limiting example of which would be 40% acetonitrile and 60% water. The eluent for the same SPE cartridge can be aqueous ethanol, a non-limiting example of which is 60% ethanol and 40% water. In one embodiment when the SPE is C18, an ethanol-based organic solvent for step (iii) and for elution can be used. As a non-limiting example 30-40% ethanol in water for the solvent for step (iii) followed by ethanol elution, which can be less than 100% ethanol.

In one embodiment said wash solution comprising an organic solvent of step (c)(iii) comprises 30-60% of said organic solvent in water.

In one embodiment said wash solution comprising an organic solvent of step (c)(iii) comprises acetonitrile, methanol or ethanol.

In one embodiment said wash solution comprising an organic solvent is an aqueous solution of acetonitrile.

In one embodiment said aqueous solution of acetonitrile comprises 30-50% acetonitrile, preferably 40% acetonitrile.

In one embodiment said wash solution comprising an organic solvent is an aqueous solution of methanol.

In one embodiment said aqueous solution of methanol comprises 20-80% methanol, preferably 30-50% methanol.

In one embodiment said wash solution comprising an organic solvent is an aqueous solution of ethanol.

In one embodiment said aqueous solution of ethanol comprises 35-55% ethanol.

In one embodiment said elution solution of step (v) comprises 40-100% ethanol.

In one embodiment said elution solution of step (v) comprises 50-80% ethanol, preferably 65-75% ethanol and most preferably 70% ethanol.

In one embodiment said elution solution of step (v) comprises 30-50% ethanol, preferably 40-50% ethanol, most preferably 45% ethanol.

In one embodiment said ethanol of step (v) comprises 50-100% ethanol.

In one embodiment said hydrolysing reagent is added to said crude reaction mixture in step (b).

In one embodiment said hydrolysing reagent is comprised in said water of step (ii).

In one embodiment said hydrolysing reagent is comprised in said water of step (iv) and steps (ii) and (iii) are repeated before carrying out step (v).

In one embodiment said SPE cartridge is selected from a tC18 SPE cartridge and a mixed mode SPE cartridge.

In one embodiment said SPE cartridge is a tC18 cartridge.

In one embodiment said method further comprises a step before step (v) of passing a solution comprising an organic solvent through said SPE cartridge and a fluidly connected second SPE cartridge and wherein step (v) is carried out with said second SPE cartridge.

In one embodiment, said SPE cartridge and said second SPE cartridge are selected from Affinisep "P3 polymer", Waters tC18 and UCT C18.

In one embodiment, said hydrolysing reagent is acidic. Any suitable acid may be used. In one embodiment said acidic hydrolysing reagent comprises hydrochloric acid, sulphuric acid or phosphoric acid.

In one embodiment, said acidic hydrolysing reagent is HCl.

In one embodiment, said hydrolysing reagent is alkaline. Any suitable base may be used. In one embodiment, alkoxide, alkali metal hydroxides, or thiooxide bases can be used. In a further embodiment, the base is selected from the group consisting of sodium hydroxide, potassium hydroxide, sodium hydride, sodium thiomethoxide, sodium ethoxide, ammonia/ammonium hydroxide and sodium methoxide.

In one embodiment, said alkaline hydrolysing reagent is selected from NaOH, $NH_4OH$ and NaOMe. In another embodiment, said alkaline hydrolysing reagent is NaOH.

In one embodiment, step (c) includes prior to step (i) passing said diluted crude reaction mixture through a separate SPE cartridge configured to retain lipophilic components. In one embodiment said separate SPE cartridge is selected from a tC18 cartridge, or a polymeric cartridge from Affinisep.

In one embodiment, step (c) includes following step (v) passing said purified solution through a separate SPE cartridge configured to retain lipophilic components.

In one embodiment of the method of the invention (2,2,6,6-Tetramethylpiperidin-1-yl)oxyl (TEMPO) is included in reacting step (a). In one embodiment TEMPO is present in a molar ratio to the precursor compound of between 0.01:1 and 5:1, preferably between 0.1:1 and 2:1, most preferably between 0.4:1 and 0.6:1, especially preferably around 0.5:1, e.g. 0.56:1.

The method of the invention can be carried out using an automated synthesizer apparatus. By the term "automated synthesizer" is meant an automated module based on the principle of unit operations as described by Satyamurthy et al (1999 Clin Positr Imag; 2(5): 233-253). The term "unit operations" means that complex processes are reduced to a series of simple operations or reactions, which can be applied to a range of materials. Such automated synthesizers are commercially available from a range of suppliers including: GE Healthcare; CTI Inc; Ion Beam Applications S. A. (Chemin du Cyclotron 3, B-1348 Louvain-La-Neuve, Belgium); Raytest (Germany) and Bioscan (USA).

An exemplary automated synthesizer carries out a radio-synthesis by means of a cassette. By the term "cassette" is meant a piece of apparatus designed to fit removably and interchangeably onto the automated synthesizer apparatus in such a way that mechanical movement of moving parts of the synthesizer controls the operation of the cassette from outside the cassette. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated synthesizer. External rotation of the arm thus controls the opening or closing of the valve when the cassette is attached to the automated synthesizer. Additional moving parts of the automated synthesizer are designed to clip onto syringe plunger tips, and thus raise or depress syringe barrels.

A typical cassette has several positions for reagents and several suitable for attachment of syringe vials of reagents or chromatography cartridges (e.g. SPE). The cassette always comprises a reaction vessel. Such reaction vessels are preferably 1 to 10 $cm^3$, most preferably 2 to 5 $cm^3$ in volume and are configured such that 3 or more ports of the cassette are connected thereto, to permit transfer of reagents or solvents from various ports on the cassette. Preferably the cassette has 15 to 40 valves in a linear array, most preferably 20 to 30, with 25 being especially preferred. The valves of the cassette are preferably each identical, and most preferably are 3-way valves. The cassettes are designed to be suitable for radiopharmaceutical manufacture so are manufactured from materials of pharmaceutical grade and ideally also resistant to radiolysis.

In one embodiment the cassette is a disposable, single use cassette which comprises all the reagents, reaction vessels and apparatus necessary to carry out the method of the invention.

The cassette approach has the advantages of simplified set-up, reduced risk of operator error; improved GMP (Good Manufacturing Practice) compliance; multi-tracer capability; rapid change between production runs; pre-run automated diagnostic checking of the cassette and reagents; automated barcode cross-check of chemical reagents vs. the synthesis to be carried out; reagent traceability; single-use and hence no risk of cross-contamination, tamper and abuse resistance.

Therefore, in another aspect the present invention provides a cassette for carrying out the method as defined in claim 1 where said cassette comprises:
  i) a vessel containing the precursor compound as defined in claim 1;
  ii) a vessel containing water;
  iii) one or more SPE cartridges;
  iv) a vessel containing a solution comprising an organic solvent;
  v) a vessel containing a solution comprising ethanol;
  vi) a vessel containing a hydrolysing reagent;
  vii) a reaction vessel;
  viii) means for eluting the vessel of (i) with a suitable source of $^{18}$F;
  ix) means to transfer the precursor compound and suitable source of $^{18}$F to the reaction vessel;
  x) means to transfer the crude reaction mixture as defined in claim 1 to said one or more SPE cartridges;
  xi) means to selectively transfer said water, said solution comprising an organic solvent and said solution comprising ethanol to said one or more SPE cartridges; and,
  xii) means to transfer said purified compound of Formula II as defined in claim 1 to a product collection vial.

In one embodiment the cassette of the invention further comprises (x) a vessel containing TEMPO.

In one embodiment of the cassette of the invention the vessel containing the precursor compound contains the precursor compound in acetonitrile along with TEMPO in an amount as recited hereinabove for the method of the invention.

Any feature of the cassette already recited in connection herein with the method of the invention has the same embodiments as described herein for the method of the invention.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

BRIEF DESCRIPTION OF THE EXAMPLES

Example 1 describes the radiosynthesis of crude [18F]Flurpiridaz.
Example 2 describes the radiosynthesis of crude [18F]Flurpiridaz with the addition of TEMPO.
Examples 3 and 4 describe the radiosynthesis of [18F]Flurpiridaz with SPE purification.
Example 5 describes the automated synthesis and purification of [$^{18}$F]Flurpiridaz.
Example 6 describes alternative ways for the radiosynthesis of [18F]Flurpiridaz with SPE purification.

LIST OF ABBREVIATIONS USED IN THE EXAMPLES

EtOH ethanol
HPLC high performance liquid chromatography
MeCN acetonitrile
PBS phosphate buffered saline
QMA quaternary methyl ammonium
RAC radioactive concentration
SPE solid phase extraction
TEMPO (2,2,6,6-Tetramethylpiperidin-1-yl)oxyl

EXAMPLES

Example 1: Radiosynthesis of Crude [$^{18}$F]Flurpiridaz

[$^{18}$F]-fluoride (ca. 100 GBq) was produced using a GE Medical Systems PETtrace cyclotron with a silver target via the [$^{18}$O](p,n) [$^{18}$F] nuclear reaction. Total target volumes of 3.2-4.8 mL were used. The radiofluoride was trapped on a Waters QMA cartridge (pre-conditioned with carbonate), and the fluoride was eluted with a solution of tetrabutylammnonium hydrogen carbonate (22 mg) in water (100 µL) and acetonitrile (400 µL). Nitrogen was used to drive the solution off the QMA cartridge to the reaction vessel. The [$^{18}$F]fluoride was dried for 9 minutes at 120° C. under a steady stream of nitrogen and vacuum. The precursor (10.2 mg, synthesized according to known methods) in MeCN (1.7 mL) was added to the dried [$^{18}$F]-fluoride and the reaction mixture was heated at 120° C. for 10 minutes. The crude product was diluted with water (9.3 mL) and analysed by HPLC.

The % of [$^{18}$F]Flurpiridaz in the crude product was 81% with 13% of a late eluting radiolysis product (FIG. 1). In once instance of the radiosynthesis the inventors observed only 72% [$^{18}$F]Flurpiridaz.

Example 2: Radiosynthesis of Crude [$^{18}$F]Flurpiridaz with the Addition of TEMPO

[$^{18}$F]-fluoride (ca. 100 GBq) was produced using a GE Medical Systems PETtrace cyclotron with a silver target via the [$^{18}$O](p,n) [$^{18}$F] nuclear reaction. Total target volumes of 3.2-4.8 mL were used. The radiofluoride was trapped on a Waters QMA cartridge (pre-conditioned with carbonate), and the fluoride was eluted with a solution of tetrabutylammnonium hydrogen carbonate (22 mg) in water (100 µL) and acetonitrile (400 µL). Nitrogen was used to drive the solution off the QMA cartridge to the reaction vessel. The [$^{18}$F]-fluoride was dried for 9 minutes at 120° C. under a steady stream of nitrogen and vacuum. A mixture of the precursor (10.2 mg) and TEMPO (1.7 mg) in MeCN (1.7 mL) was added to the dried [$^{18}$F]-fluoride and the reaction mixture was heated at 120 C for 10 minutes. The crude product was diluted with water (9.3 mL) and analysed by HPLC.

The % of [$^{18}$F]Flurpiridaz in the crude product was 92% with 1% of the late eluting radiolysis product. The addition of TEMPO to the labelling reaction reduces the amount of the late eluting radiolysis product (FIG. 1). The present inventors deduce from these results that even when carried out at high activity the addition of TEMPO to the radiolabelling reaction acts to reduce the late eluting radiolysis product.

Example 3: Radiosynthesis of [$^{18}$F]Flurpiridaz with EtOH-Based SPE Purification

Figure 2:
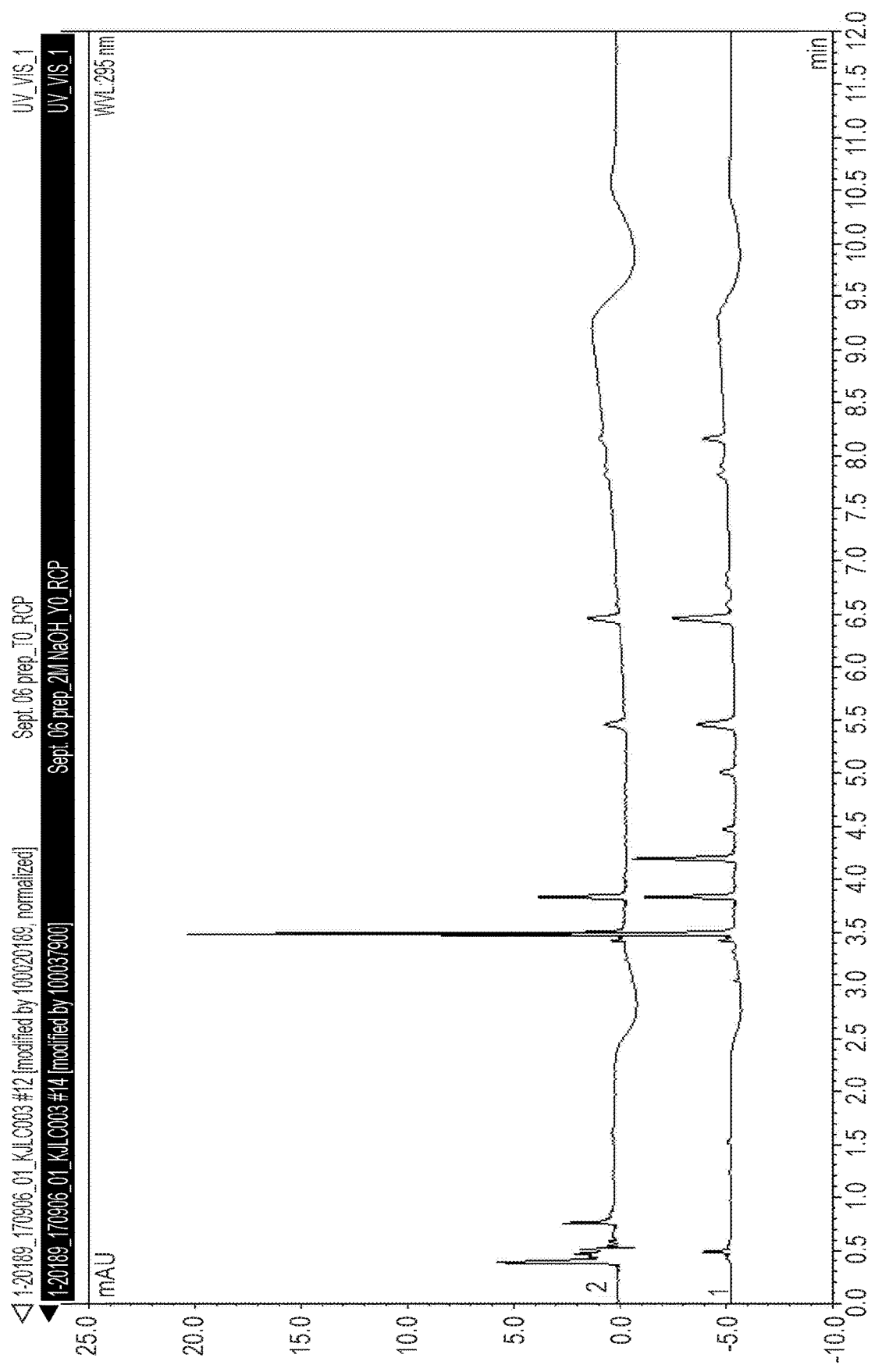
FIG. 2: Comparison of crude product with (top) and without (bottom) hydrolysis with NaOH post labelling reaction. The species in the 4-5 minute region are almost completely removed by the hydrolysis reaction.

[$^{18}$F]-fluoride (ca. 100 GBq) was produced using a GE Medical Systems PETtrace cyclotron with a silver target via the [$^{18}$O](p,n) [$^{18}$F] nuclear reaction. Total target volumes of 3.2-4.8 mL were used. The radiofluoride was trapped on a Waters QMA cartridge (pre-conditioned with carbonate), and the fluoride was eluted with a solution of tetrabutylammonium hydrogen carbonate (22 mg) in water (100 μL) and acetonitrile (400 μL). Nitrogen was used to drive the solution off the QMA cartridge to the reaction vessel. The [$^{18}$F]fluoride was dried for 9 minutes at 120° C. under a steady stream of nitrogen and vacuum. The precursor (10.2 mg) in MeCN (1.7 mL) was added to the dried [$^{18}$F]-fluoride and the reaction mixture was heated at 120 C for 10 minutes. The crude product was diluted with 2 M NaOH (1.3 mL) and water (4 mL) and left to stand for 60 seconds (see FIG. 2 for comparison of with and without NaOH hydrolysis). The crude product was then loaded onto a tC18 SPE cartridge (Waters, product number WAT036800) and purified using the method described below.

The SPE cartridge was washed with water (30 mL) to wash away the acetonitrile, NaOH and hydrophilic chemical and radiochemical impurities. Then the SPE cartridge was washed with a 35% ethanol solution in water (25 mL) to remove the hydroxy impurity. After this, the first SPE cartridge was connected in series to a second SPE cartridge (Waters, product number WAT036800) and the two were washed with a 40% ethanolic water solution (14 mL) followed by a stream of nitrogen to transfer the [$^{18}$F]Flurpiridaz onto the second cartridge and trap the more lipophilic chemical and radiochemical impurities. The second SPE cartridge was then eluted with a 70% ethanolic solution (3 mL) to elute the [$^{18}$F]Flurpiridaz into the product vial. The 25 mL product vial was composed of water (23 mL), ethanol (2 mL) and ascorbic acid (50 mg/mL). See FIG. 3 for a chromatogram of the SPE purified product with and without ascorbic acid present.

Figure 3:
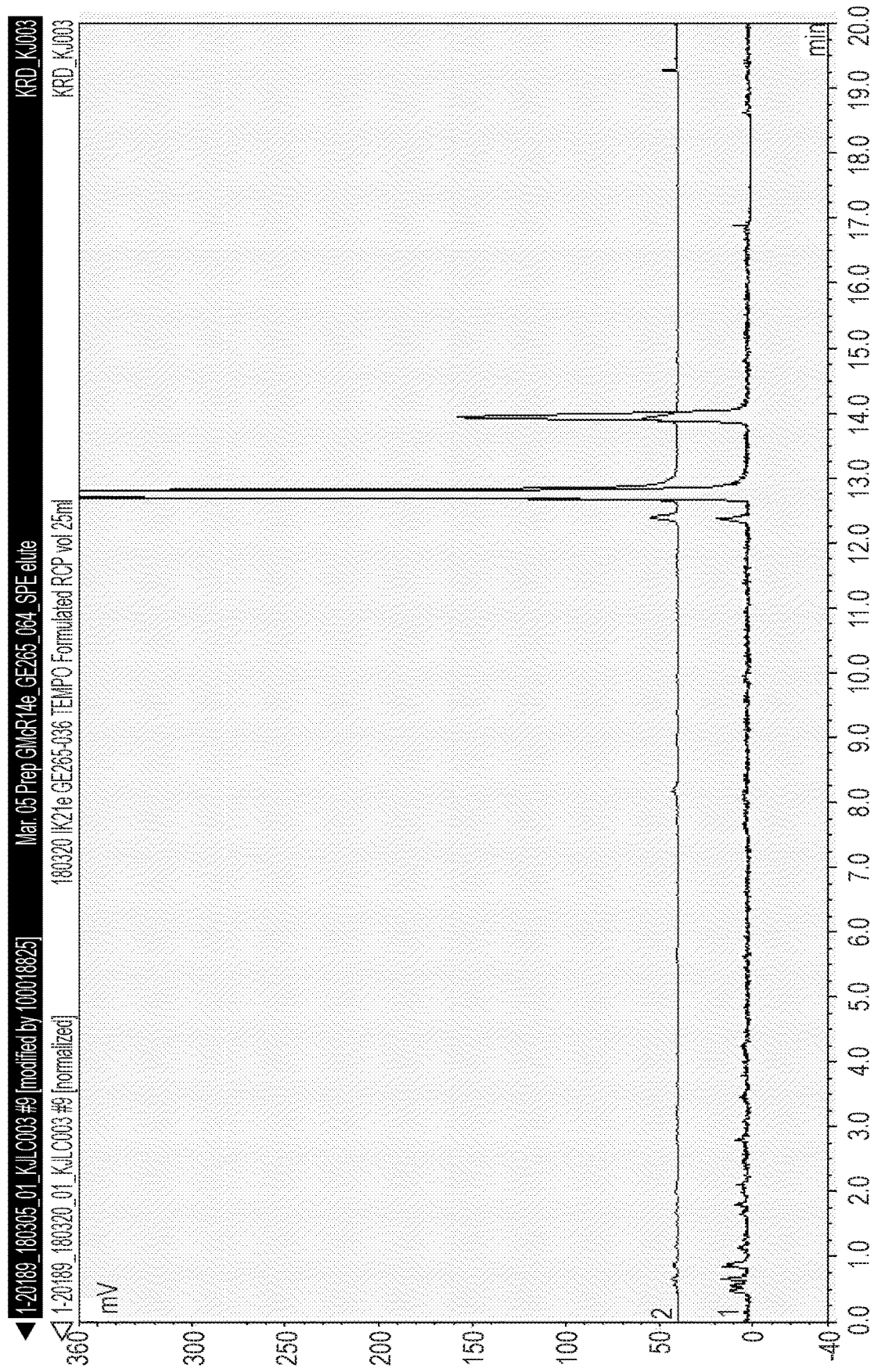
FIG. 3: Comparison of SPE purified product with (top) and without (bottom) ascorbic acid present in the product vial.

The non decay corrected yield was 43%, resulting in a product with an RAC of 1,800 MBq/mL. The RCP of the final product was 97%. Two radiolysis products were observed (1% and 2% respectively). When ascorbic acid is excluded from the product vial, the RCP is 85-88% (FIG. 3).

Example 4: Radiosynthesis of [$^{18}$F]Flurpiridaz with EtOH-Based SPE Purification

[$^{18}$F]-fluoride (ca. 100 GBq) was produced using a GE Medical Systems PETtrace cyclotron with a silver target via the [$^{18}$O](p,n) [$^{18}$F] nuclear reaction. Total target volumes of 3.2-4.8 mL were used. The radiofluoride was trapped on a Waters QMA cartridge (pre-conditioned with carbonate), and the fluoride was eluted with a solution of tetrabutylammonium hydrogen carbonate (22 mg) in water (100 μL) and acetonitrile (400 μL). Nitrogen was used to drive the solution off the QMA cartridge to the reaction vessel. The [$^{18}$F]fluoride was dried for 9 minutes at 120° C. under a steady stream of nitrogen and vacuum. The precursor (10.2 mg) in MeCN (1.7 mL) was added to the dried [$^{18}$F]-fluoride and the reaction mixture was heated at 120 C for 10 minutes. The crude product was diluted with 2 M NaOH (1.3 mL) and water (4 mL) and left to stand for 60 seconds (see FIG. 2 for comparison of with and without NaOH hydrolysis). The crude product was then loaded onto a tC18 SPE cartridge (Waters, product number WAT036800) and purified using the method described below.

The SPE cartridge was washed with water (30 mL) to wash away the acetonitrile, NaOH and hydrophilic chemical and radiochemical impurities. Then the SPE cartridge was washed with a 40% acetonitrile solution in water (10 mL) to remove the hydroxy impurity. After this, the first SPE cartridge was connected in series to a second SPE cartridge (Waters, product number WAT036800) and the two were washed with 40% acetonitrile (25 mL) followed by a stream of nitrogen to transfer the [$^{18}$F]Flurpiridaz onto the second cartridge and trap the more lipophilic chemical and radiochemical impurities. The second SPE cartridge was then eluted with a 45% ethanolic solution (7 mL) to elute the [$^{18}$F]Flurpiridaz into the product vial. The 45 mL product vial was composed of water (42 mL), ethanol (3 mL) and ascorbic acid (50 mg/mL).

The non decay corrected yield was 40-44%, resulting in a product with an RAC of 1,700-2,000 MBq/mL. The RCP of the final product was 97-98%. Two radiolysis products were observed (1% and 1-2% respectively).

Example 5: Automated Synthesis and Purification of [$^{18}$F]Flurpiridaz

A FASTlab™ automated synthesizer (GE Healthcare Ltd) with cassette was used. The tC18 cartridge was obtained from Waters Limited (address as above). Precursor 1 was reacted with [$^{18}$F]fluoride on the FASTlab™ according to Example 3 to give [$^{18}$F]Flurpiridaz.
Purification.

Figure 4:
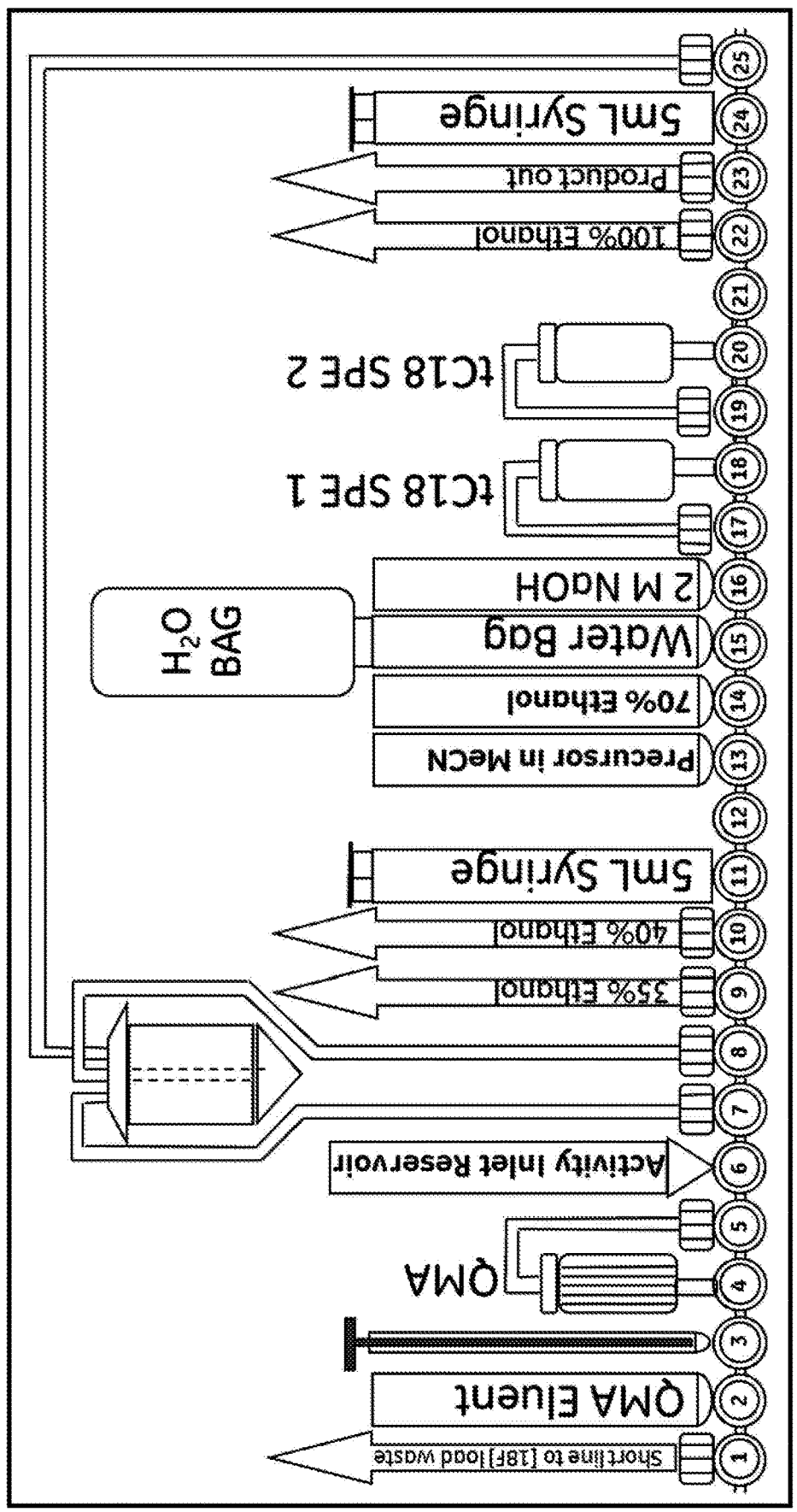
FIG. 4 shows the layout of a FASTlab™ cassette suitable for carrying out the method of the invention.

The cassette configuration is given in FIG. 4. Three external solvent vials are used on the cassette for the SPE purification in addition to the formulation vial:
Position 9=35% ethanol (or 40% acetonitrile) in water;
Position 10=40% ethanol (or 45% ethanol) in water;
Position 22=100% ethanol
Position 23=23 mL water for formulation.
Other Cassette Positions:
Position 14=70% ethanol in water (or blank)
Position 17: Tubing to the tC18 cartridge (SPE1) in Position 18;
Position 18: tC18 cartridge;
Position 19: Tubing to the tC18 cartridge (SPE2) in Position 18;
Position 20: tC18 cartridge;
FASTlab™ Procedure.

In the following, P refers to the Position of the cassette. S2 and S3 refer to syringe 2 and syringe 3:
(i) the first part of the purification process was conditioning with full S2 fill with ethanol from P22, followed by a full S2 fill of water from P15.
(ii) the hydrolysed crude product was diluted with water to 7 mL total volume in S2 and then slowly trapped onto SPE1.
(iii) SPE1 was washed with 5×5 mL 35% ethanol (or 10-14 mL 40% acetonitrile) from position 9 via S2.

(iv) SPE1 and SPE2 were washed with 3×5 mL 40% ethanol (or 21-25 mL 40% acetonitrile) from position 10 via S2 to transfer [$^{18}$F]Flurpiridaz from SPE1 onto SPE2.
(v) the product was eluted from SPE2 with 70% ethanol (or 45% ethanol if acetonitrile method) solution from P14.
(vi) SPE2 was dried with a flow of nitrogen to ensure all of the product was transferred to the product collection vial (FIG. 4)

Example 6: Radiosynthesis of [$^{18}$F] Flurpiridaz with MeCN-Based SPE Purification

[$^{18}$F]-fluoride (ca. 100 GBq) is produced using a GE Medical Systems PETtrace cyclotron with a silver target via the [$^{18}$O](p,n) [$^{18}$F] nuclear reaction. Total target volumes of 3.2-4.8 mL are used. The radiofluoride is trapped on a Waters QMA cartridge (pre-conditioned with carbonate), and the fluoride is eluted with a solution of tetrabutylammnonium hydrogen carbonate (22 mg) in water (100 μL) and acetonitrile (400 μL). Nitrogen is used to drive the solution off the QMA cartridge to the reaction vessel.

The [$^{18}$F]fluoride is dried for 9 minutes at 120° C. under a steady stream of nitrogen and vacuum. The precursor (10.2 mg) in MeCN (1.7 mL) is added to the dried [$^{18}$F]-fluoride and the reaction mixture is heated at 120° C. for 10 minutes. The crude product is diluted with water (5.3 mL) and loaded onto a tC18 SPE cartridge (Waters, product number WAT036800) and is purified using the method described below.

Sodium hydroxide (2 M, ca. 3 mL) is passed through the SPE cartridge at a slow flow rate to hydrolyse the crude product. The SPE cartridge is then washed with aqueous solution (14 mL) to wash away the acetonitrile, NaOH and hydrophilic chemical and radiochemical impurities. Then the SPE cartridge is washed with a 40% acetonitrile solution in water (10.5 mL) to remove the hydroxy impurity. In an alternative, the SPE cartridge could be washed with NaOH here either instead of or in addition to the earlier NaOH step. After this, the first SPE cartridge is connected in series to a second SPE cartridge (Waters, product number WAT036800) and the two are washed with further 40% acetonitrile water solution (24.5 mL) followed by a stream of nitrogen to transfer the [$^{18}$F]Flurpiridaz onto the second cartridge and trap the more lipophilic chemical and radiochemical impurities. The second SPE cartridge (optionally washed before ethanol elution) is then eluted with a 45% ethanolic solution (9 mL, 3-9 mL fraction collected in product vial) followed by water (4 mL) and a stream of nitrogen to elute the [$^{18}$F]Flurpiridaz into the product vial.

The invention claimed is:
1. A method comprising:
(a) reacting in acetonitrile a precursor compound of Formula I:

BTM-LINKER-LG        (I)

wherein:
BTM is a biological targeting moiety;
LINKER is an alkylene or an alkoxyalkylene; and
LG is a sulfonate-containing leaving group
with $^{18}$F-fluoride to obtain a crude reaction mixture comprising an $^{18}$F-labelled compound of Formula II:

BTM-LINKER-18F        (II)

wherein BTM and LINKER are as defined for Formula I;

(b) diluting the crude reaction mixture obtained in step (a) to obtain a diluted crude reaction mixture;
(c) purifying the diluted crude reaction mixture obtained in step (b) using one or more solid phase extraction (SPE) cartridges to obtain a purified compound of Formula II where said purifying comprises the sequential steps of:
(i) transferring said diluted crude reaction mixture to an SPE cartridge;
(ii) optionally passing water through said SPE cartridge;
(iii) passing a wash solution comprising an organic solvent through said SPE cartridge;
(iv) optionally passing water through said SPE cartridge to remove said organic solvent; and
(v) passing an elution solution comprising ethanol through said SPE cartridge to elute said compound of Formula I from said SPE cartridge;
wherein step (b) includes adding a hydrolyzing reagent to said crude reaction mixture and/or said water of step (ii) and/or step (iv) comprises a hydrolyzing reagent; and
wherein said precursor compound of Formula I is a compound having Formula Ia:

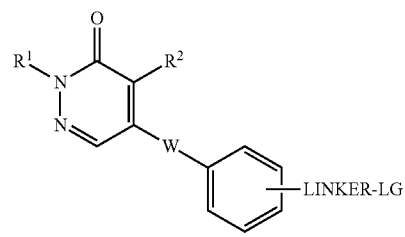

(Ia)

and said $^{18}$F-labelled compound of Formula II is a compound of Formula IIa:

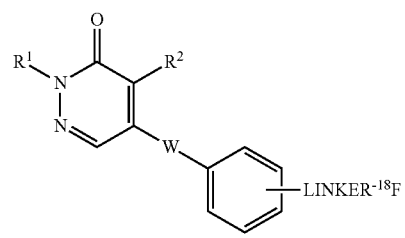

(IIa)

wherein:
$R^1$ is an optionally substituted $C_{1-6}$ alkyl;
$R^2$ is hydrogen or halo;
W is an optionally substituted alkylene or heteroalkylene; and
LINKER and LG are as defined for Formula I.
2. The method as defined in claim 1 wherein $R^1$ is $C_{1-6}$ alkyl.
3. The method as defined in claim 1 wherein $R^1$ is methyl, ethyl, propyl, n-butyl, s-butyl, or t-butyl.
4. The method as defined in claim 1 wherein $R^2$ is halo.
5. The method as defined in claim 1 wherein $R^2$ is chloro.
6. The method as defined in claim 1 wherein W is heteroalkylene.
7. The method as defined in claim 1 wherein W is alkoxyalkylene.

8. The method as defined in claim 1 wherein said compound of Formula I is:

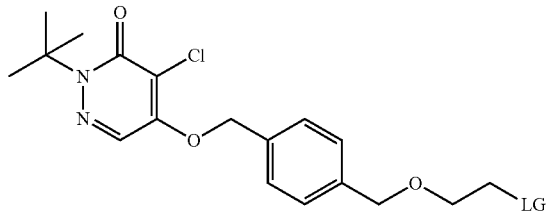

wherein LG is a sulfonate-containing leaving group; and said compound of Formula II is:

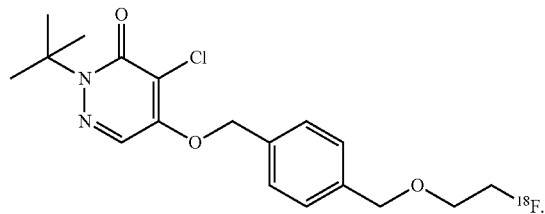

9. The method as defined in claim 1 wherein LG is selected from mesylate, tosylate, triglate, nosylate, or 1,2-cyclic sulfate.

10. The method as defined in claim 9 wherein LG is tosylate.

11. The method as defined in claim 1 wherein said wash solution comprising an organic solvent of step (c) (iii) comprises 20-80% of said organic solvent in water.

12. The method as defined in claim 1 wherein said wash solution comprising an organic solvent of step (c) (iii) comprises 30-60% of said organic solvent in water.

13. The method as defined in claim 1 wherein said wash solution comprising an organic solvent of step (c) (iii) comprises acetonitrile, methanol or ethanol.

14. The method of claim 13, wherein the wash solution comprising are organic solvent of step (c) (iii) is an aqueous solution of acetonitrile comprising 40% acetonitrile.

15. The method of claim 13, wherein the elution solution of step (v) comprises 45% ethanol.

16. The method of claim 1, wherein the hydrolyzing agent is NaOH.

17. The method of claim 1, further comprising the step of adding ascorbic acid to the purified compound after step (v) of step (c).

18. A cassette for carrying out the method as defined in claim 1 comprising:
(i) a vessel containing a precursor compound of Formula I:

BTM-LINKER-LG (I)

wherein:
BTM is a biological targeting moiety;
LINKER is an alkylene or an alkoxyalkylene, and
LG is a sulfonate-containing leaving group;
(ii) a vessel containing water;
(iii) one or more SPE cartridges;
(iv) a vessel containing a solution comprising an organic solvent;
(v) a vessel containing a solution comprising ethanol;
(vi) a vessel containing a hydrolyzing reagent;
(vii) a reaction vessel;
(viii) means for eluting the vessel of (i) with a suitable source of $^{18}F$;
(ix) means to transfer the precursor compound and suitable source of $^{18}F$ to the reaction vessel;
(x) means to transfer the crude reaction mixture to said one or more SPE cartridges, the crude reaction mixture comprising an $^{18}F$ labelled compound of Formula II:

BTM-LINKER-$^{18}F$ (II)

wherein BTM and LINKER are as defined for Formula I;
(xi) means to selectively transfer said water, said solution comprising an organic solvent and said solution comprising ethanol to said one or more SPE cartridges; and
(xii) means to transfer said purified compound of Formula II to a product collection vial.

19. The cassette as defined in claim 18 which further comprises (x) a vessel containing TEMPO.

20. The cassette as defined in claim 18 wherein said vessel containing the precursor compound contains the precursor compound in acetonitrile along with.

21. The cassette of claim 18, wherein the product collection vial contains ascorbic acid.

* * * * *